US00PP15153P3

(12) United States Plant Patent
López

(10) Patent No.: US PP15,153 P2
(45) Date of Patent: Sep. 21, 2004

(54) STRAWBERRY PLANT NAMED 'PLAHUELFRE'

(50) Latin Name: *Fragaria L.*
Varietal Denomination: Plahuelfre

(75) Inventor: José Miguel Arias López, Tudela (ES)

(73) Assignee: Plantas de Navarra, S.A. (ES)

( * ) Notice: Subject to any disclaimer, the term of this patent is extended or adjusted under 35 U.S.C. 154(b) by 0 days.

(21) Appl. No.: 10/128,892

(22) Filed: Apr. 24, 2002

(65) Prior Publication Data

US 2003/0041362 P1 Feb. 27, 2003

(30) Foreign Application Priority Data

May 25, 2001 (ES) ..... 20010152
Sep. 21, 2001 (EP) ..... 2001/1515

(51) Int. Cl.[7] ..... A01H 5/00
(52) U.S. Cl. ..... Plt./208
(58) Field of Search ..... Plt./208

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new strawberry plant variety characterized by is inflorescence that appears level with the foliage and abundant production of red colored, conical shaped, firm, large sized fruit.

8 Drawing Sheets

Classification: The present invention relates to a new *Fragaria L.* plant.

Variety denomination: The new plant has the varietal denomination 'Plahuelfre'.

BACKGROUND OF THE INVENTION

The new variety of strawberry was created in a breeding program by crossing two parents; in particular, by crossing as seed parent an undistributed strawberry variety designated 9244 and as pollen parent an undistributed strawberry variety designated 86-032. Both parental varieties are proprietary and have not been commercialized. Both parents are undistributed and unpatented strawberry varieties.

The resulting seedling of the new variety was grown and asexually propagated by runners in Soria, Spain, 3°W., 41°N., 3000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Plahuelfre'. Among the characteristics which are believed to distinguish the new variety from other varieties are a combination of traits which include inflorescence that appears level with the foliage and abundant production of red colored, conical-shaped, firm large fruit.

COMPARISON TO CLOSEST VARIETY

The new variety is closest to the variety 'Cartuno' (U.S. Plant Pat. No. P.P. 8,623), but is distinguished therefrom by the following characteristics possessed by 'Plahuelfre' which are different than, or not possessed by, 'Cartuno'.

1. Length/width ratio of the terminal leaflet in 'Cartuno' is longer than broad, whereas in 'Plahuelfre' it is as long as broad.
2. Shape of base of the terminal leaflet in 'Cartuno' is rounded, whereas in 'Plahuelfre' it is acute.
3. Pose of hairs in the petiole of 'Cartuno' is outwards, whereas in 'Plahuelfre' it is upwards.
4. In 'Cartuno' the position of the inflorescence relative to foliage is above, whereas the inflorescence in 'Plahuelfre' is level with the foliage.
5. Size of calyx relative to corolla in the flower of 'Cartuno' is larger, whereas in 'Plahuelfre' it is same size.
6. Band without achenes in the fruit of 'Cartuno' is absent or very narrow, whereas in 'Plahuelfre' it is always narrow.
7. 'Cartuno' has orange-red to red fruit color (near 33A to 40A) with a strong glossiness, whereas the fruit of 'Plahuelfre' is a strong red fruit color (near 43A to 42A) with a weak glossiness.
8. Size of calyx in relation to fruit diameter is larger in 'Cartuno', whereas it is same size in 'Plahuelfre'.

The differences in the fruits of 'Camarosa' (U.S. Pat. No. P.P. 8,708) and the new variety are shown in FIG. 8. These differences are maintained during the harvest season.

9. Adherence of calyx in the fruit of 'Cartuno' is medium, whereas it is very strong in 'Plahuelfre'.
10. Acidity of fruit in 'Cartuno' is medium, whereas in 'Plahuelfre' it is strong.
11. 'Cartuno' has firm fruit that is smaller than 'Plahuelfre'.
12. Precocity in 'Cartuno' is smaller than in 'Plahuelfre'.

BRIEF DESCRIPTION OF ILLUSTRATIONS

The accompany photographs show typical specimens of the new variety (designated 96.09.014) in the illustrations, including fruit, foliage and flower, in color as nearly true as it is reasonably possible to make in color illustrations of this character. The plants depicted in the drawings were planted October 2000 in a farm of La Mogalla in Cartaya (Huelva), Spain. The photos were taken in March 2001.

DESCRIPTION OF THE NEW VARIETY

The following detailed description of the new variety is based upon observations taken of plants and fruits grown "underglass," i.e. undertunnel, in the farm of La Mogalla in Cartaya (Huelva), Spain, 7°W., 37°N., 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation environmental, seasonal, climatic, and cultural conditions.

PROPAGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'Plahuelfre' is a short day variety that needs an induction to flowering by chilling, such as occurs at a high elevation nursery (fresh plant) or with cold storage (referred to as a frigo). Usually a short time is sufficient. 'Plahuelfre' is self-fertile. It produces a large quantity of pollen throughout the seasons and pollination is generally good as there are very few malformed fruit.

Production: Plants described are from high elevation nursery.

Trials pursued in Cartaya (Huelva), Spain.

Date of planting: Oct. 23, 2000.

Number of repetitions: 2 .

Plants per repetition: 150.

Figure 1:
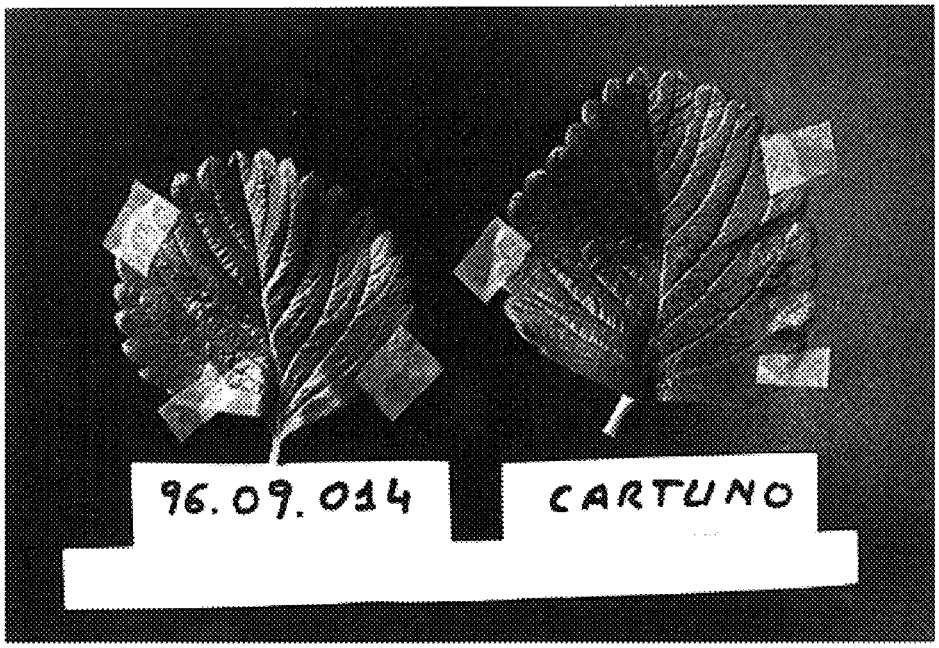
FIG. 1 shows the upper side and underside of a typical foliage of the new variety (designated 96.09.014), with an acute base shape and in which the length/width ratio is as long as broad, and a typical terminal leaflet of 'Cartuno' with a rounded base shape and in which the length/width ratio is longer than broad.
Figure 2:
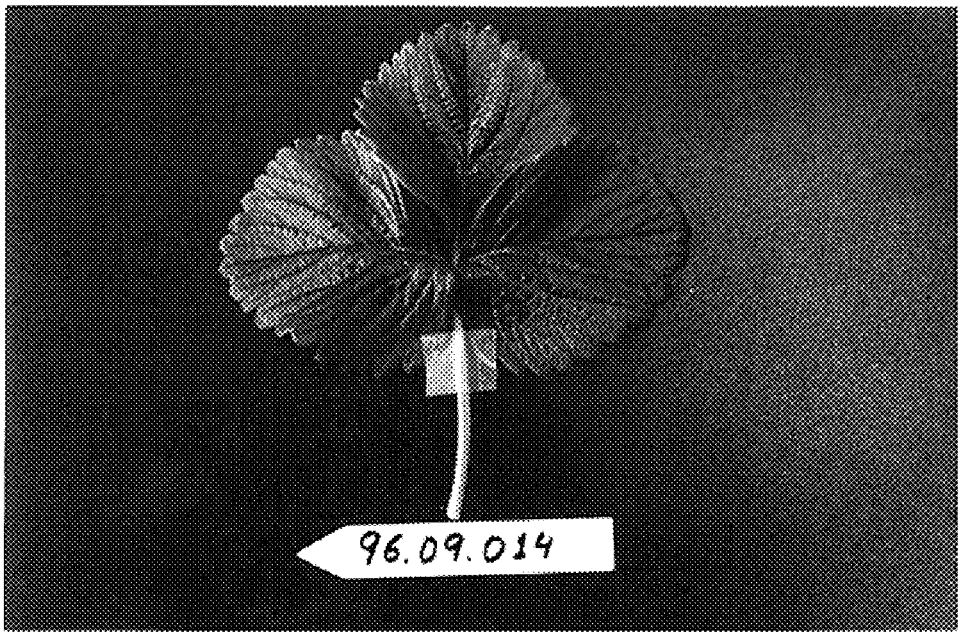
FIG. 2 shows a complete leaflet of the new variety (designated 96.09.014) and in which can be seen the acute base shape of the terminal leaflet.
Figure 3:
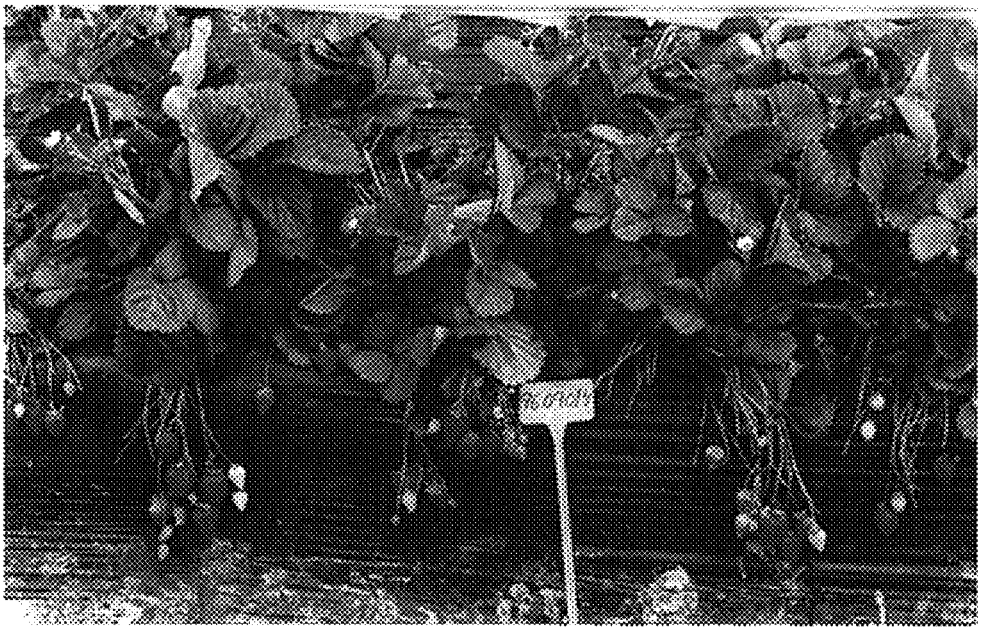
FIGS. 3 and 4 show the fruit against a background of the top surface of the foliage of the new variety (designated 96.09.014).
Figure 4:
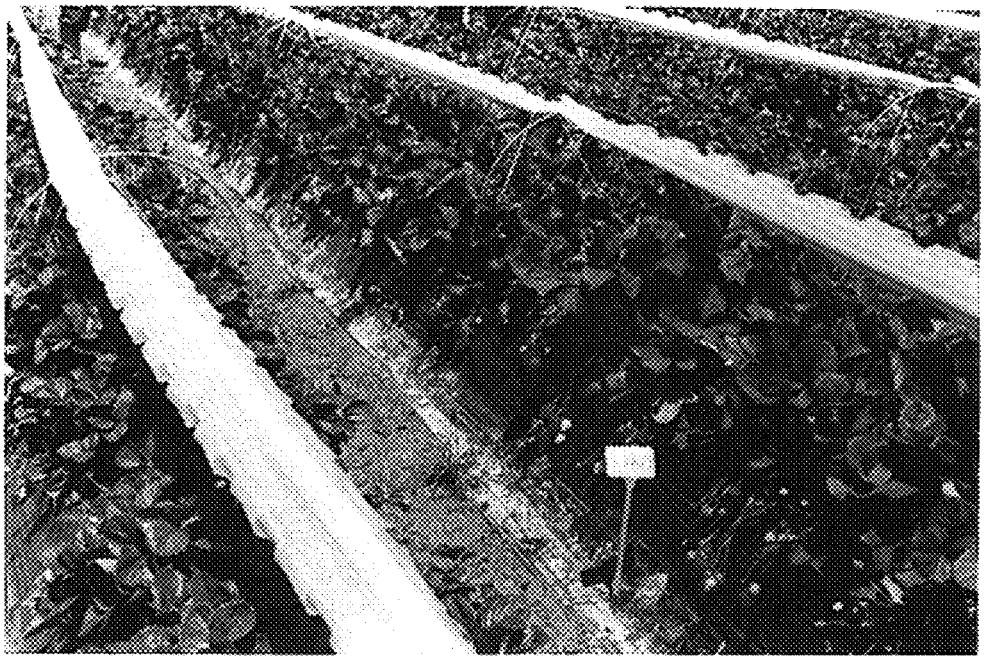
Figure 5:
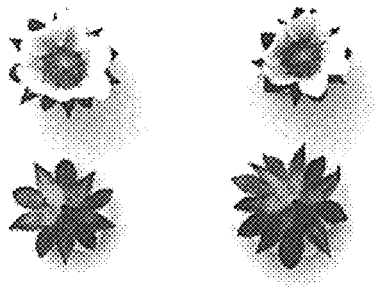
FIG. 5 shows the flower and reproductive organs of the new variety (designated 96.09.014).
Figure 6:
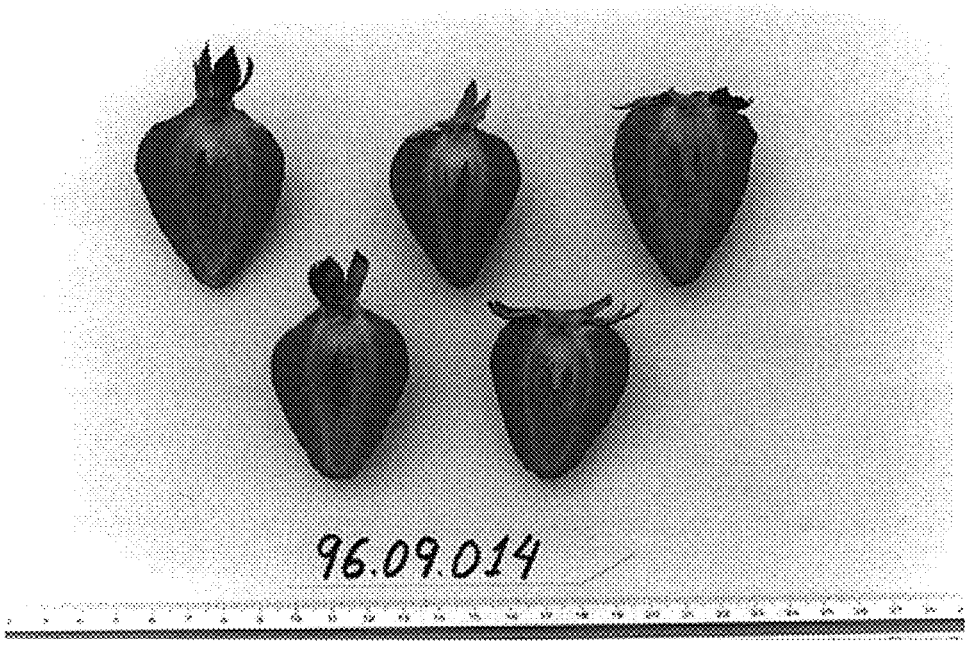
FIG. 6 shows typical fruit of the new variety (designated 96.09.014) in cross section illustrating the typical flesh and flesh coloration, conspicuous core and core cavity and conical shape.
Figure 7:
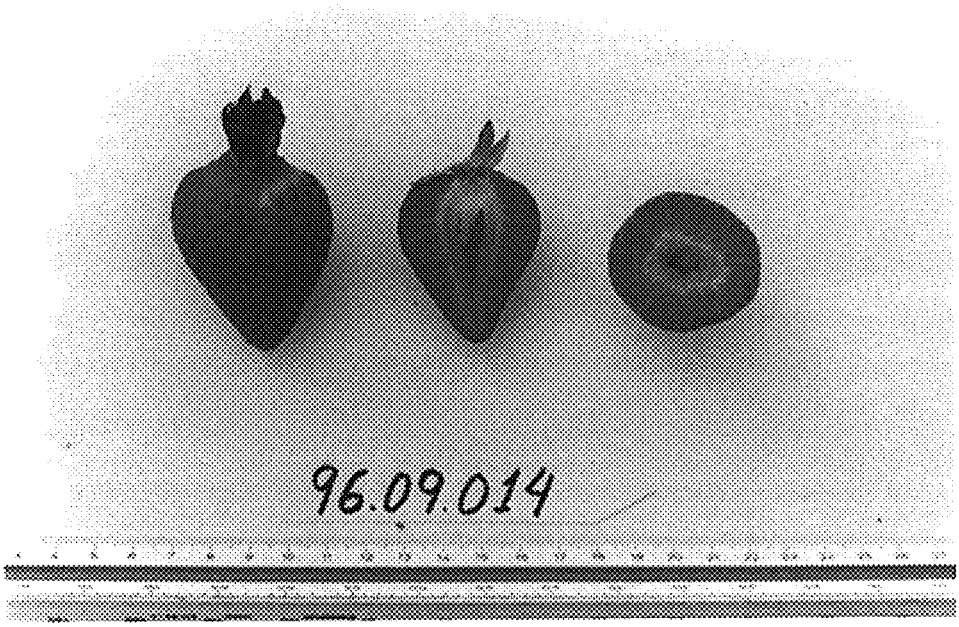
FIG. 7 shows whole and sliced, detached fruit of the new variety (designated 96.09.014) with the typical red color.
Figure 8:
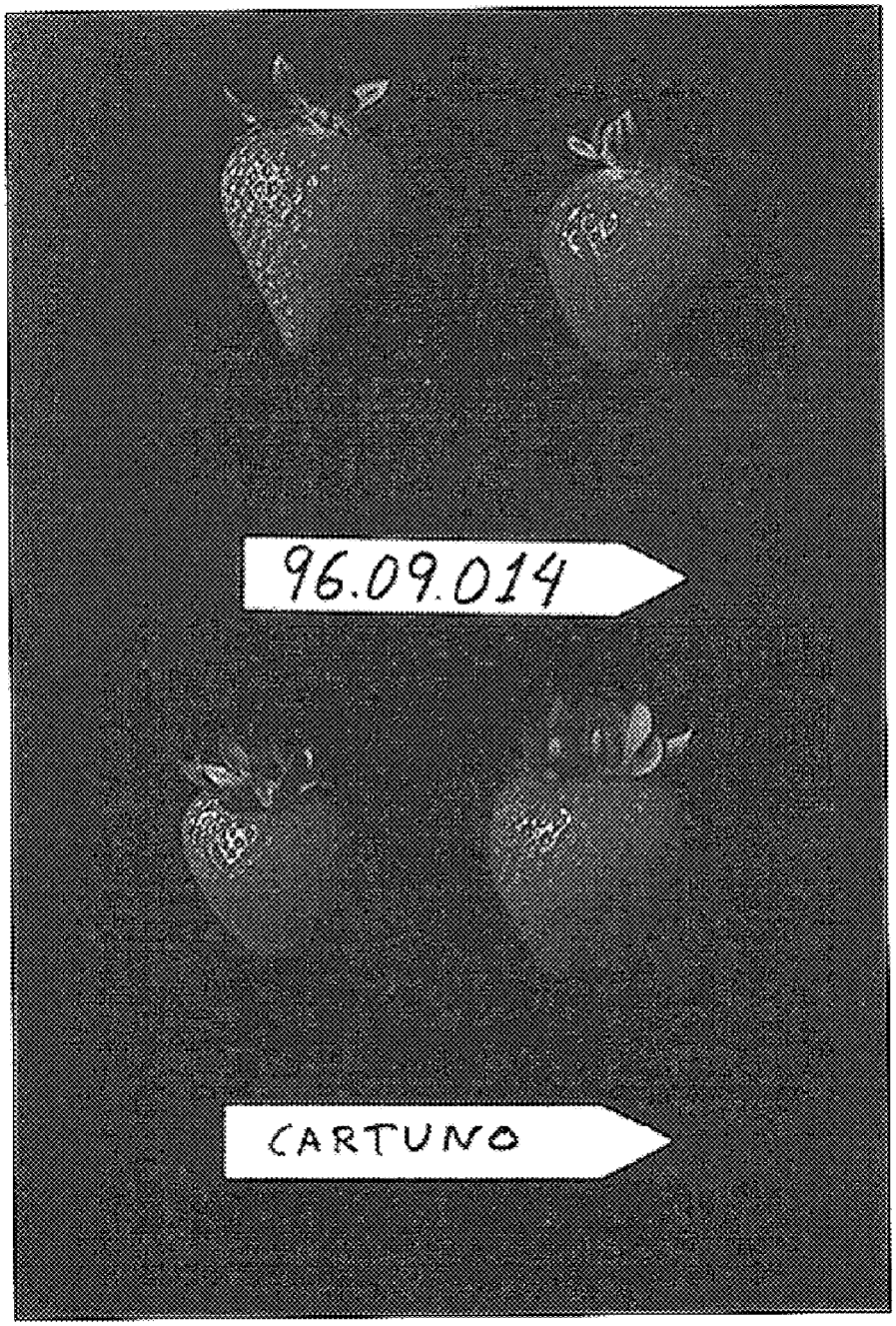
FIG. 8 shows a typical fruits of the new variety (designated 96.09.014) in which band without achenes is narrow, and a typical fruits of 'Cartuno' in which band without achenes is absent or very narrow.

Comparison with 'Cartuno': The new variety is compared with 'Cartuno' in FIG. 1 and FIG. 8.

| Accumulated production of 1st quality fruit (g/plant) | | | | |
|---|---|---|---|---|
| Variety | Feb. 23 | Mar. 28 | Apr. 24 | May 15 |
| 'CARTUNO' | 2 | 135 | 528 | 719 |
| 'CAMAROSA' | 8 | 181 | 624 | 861 |
| 'TUDNEW' | 26 | 198 | 544 | 676 |
| 'PLAHUELFRE' | 46 | 232 | 564 | 724 |

| Variety | 1st + 2nd Quality Fruit | Total | Weight (g/fruit) |
|---|---|---|---|
| 'CARTUNO' | 719 + 111 | 830 | 22–21 |
| 'CAMAROSA' | 861 + 157 | 1018 | 24–23 |
| 'TUDNEW' | 676 + 86 | 762 | 24–23 |
| 'PLAHUELFRE' | 724 + 81 | 805 | 23 –22 |

| Production total, to May 15, of First Quality Fruit (1st quality) and Second Quality Fruit (2nd quality) in g/plant | | | | |
|---|---|---|---|---|
| Variety | 1st quality | 2nd quality | TOTAL (1st quality + 2nd quality) | % 2nd quality |
| 'CARTUNO' | 719 | 111 | 830 | 13 |
| 'CAMAROSA' | 861 | 157 | 1018 | 15 |
| 'TUDNEW' | 676 | 86 | 762 | 11 |
| 'PLAHUELFRE' | 724 | 81 | 805 | 10 |

$$\% \ 2^{nd} \text{ quality} = \frac{2^{nd} \text{ quality}}{\text{TOTAL}} \times 100$$

| Weight (g/Fruit) at two dates: Mar. 28 and May 15 | | |
|---|---|---|
| Weight (g/fruit) | Mar. 28 | May 15 |
| 'CARTUNO' | 22 | 21 |
| 'CAMAROSA' | 24 | 23 |
| 'TUDNEW' | 24 | 23 |
| 'PLAHUELFRE' | 23 | 22 |

WEIGHT is shown as the average weight per fruit in First Quality Fruits.

FRUIT ANALYSIS

| | 'CAMA-ROSA' | 'PLAHUELFRE' (96.09.014) | 'CARTUNO' | 'TUD-NEW' |
|---|---|---|---|---|
| Firmness (KG) | 1.20 | 1.30 | .70 | .90 |
| Humidity & Volatile Matter (%) | 92.80 | 92.70 | 93.30 | 88.00 |
| Dry Matter (%) | 7.20 | 7.30 | 6.70 | 12.00 |
| PH (to 20°) | 3.50 | 3.60 | 3.90 | 3.60 |
| Anhydride Citric Acidity (%) | .80 | .80 | .51 | .90 |
| Soluble Solids (° Brix) | 9.50 | 8.30 | 10.90 | 8.60 |
| Maturity Index | 11.90 | 11.10 | 21.40 | 9.60 |
| Content in Ascorbic Acid (ppm) | 500 | 610 | 560 | 820 |

-continued

| | 'CAMA-ROSA' | 'PLAHUELFRE' (96.09.014) | 'CARTUNO' | 'TUD-NEW' |
|---|---|---|---|---|
| Dominant Tonality (nm) | 495 | 490 | 495 | 495 |
| Luminosity: Transmitance to 460 nm | 26.50 | 38.60 | 30.70 | 16.70 |

The following definitions apply:

Firmness: It is the fruit's resistance to penetration 0 measured in Kilograms (Kg). The measure given has been obtained by the penetrometer ROZE Mod. Arbelette, with a 50 $mm^2$ section head.

Dry Matter: It is the weight of the residual left from the trituration of the fruit after the drying process at a temperature of 103° C.+2° C. until reaching constant weight.

$$(\%)\ \text{Dry Matter} = \frac{\text{Weight Dry Matter}}{\text{Weight Fresh Matter}} \times 100$$

Humidity & Volatile Matter: Represents the content in volatile matters and water of the fruits.

$$(\%)\ \text{Humidity \& Volatile Matter} = 100 - \%\ \text{Dry Matter}$$

Maturity Index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety:

Variety: 'Plahuelfre' Breeder Ref. 96.09.014.
Classification: *Fragaria, L.*
Plant:
- *Habit.*—Globose.
- *Density.*—Medium.
- *Vigor.*—Strong.
- *Height.*—About 25 cm.
- *Width.*—About 26 cm.

Leaf:
- *Color.*—Upper side near 136A to 136B; underside near 139D to 141D.
- *Length.*—About 12 cm.
- *Width.*—About 13 cm.
- *Cross section.*—Concave.
- *Leaf surface undulation or blistering.*—Medium.
- *Number of leaflets.*—Three (3) only.

Leaf stem characteristics:
- *Color.*—Near 138D.
- *Position of hairs.*—Upwards.
- *Length.*—About 11 cm.
- *Terminal leaflet.*—Length/width ratio: As long as broad. Length: About 7.5 cm. Width: About 7.5 cm. Shape of base: Acute. Shape of teeth: Obtuse.
- *Petiole.*—Position of hairs: Upwards. Length: About 15 cm.
- *Stipule.*—Anthocyanin coloration — medium.
- *Stolons.*—Medium, about 7. Anthocyanin coloration: Medium, near 142D. Thickness: Medium, about 3 mm. Pubescence: Medium.

Inflorescence:
- *Position relative to foliage.*—Level with.
- *Flower.*—Size: Medium. Size of calyx relative to corolla: Same size. Size of inner calyx relative to outer: Larger. Spacing of petals: Overlapping.
- *Flower characteristics diameter.*—Primary flowers: About 3.5 cm. Secondary flowers: About 2.5 cm. Number of petals: Normally about 6 — no significant fragrance. Time from bloom to mature fruit (in Huelva, Spain): About 35 to 40 days. Petal Length/Width ration: As long as broad.
- *Reproductive organs stamens.*—Length about 4 to 5 mm, color near 155D to 155C. Anthers: Color near 12A to 13B. Pollen: Color near 14B to 15B. Pistils: Color near 12B to 13C.

Fruiting truss: Attitude — erect.
Fruit:
- *Ration of length/maximum width.*—Longer than broad.
- *Color.*—Near 43A to 42A.
- *Peduncle length of inflorescence stem.*—Primary fruit about 9 cm to 11 cm, secondary fruit about 6 cm to 7 cm, color near 138D to 140D.
- *Primary fruit.*—Length: About 5 cm. Width: About 4 cm.
- *Secondary fruit.*—Length: About 4.5 cm. Width: About 3.5 cm. Size: Medium. Predominant shape: Conical.
- *Difference in shapes between primary and secondary fruits.*—Moderate.
- *Bank without achenes.*—Narrow.
- *Unevenness of surface.*—Weak.
- *Color.*—Near 43A to 42A.
- *Evenness of color.*—Even.
- *Glossiness.*—Medium.
- *Insertion of achenes.*—Below surface.
- *Insertion of calyx.*—Level.
- *Pose of the calyx segments.*—Reflexed.
- *Size of calyx in relation to fruit diameter.*—Same size.
- *Adherence of calyx.*—Strong.
- *Firmness.*—Firm.
- *Color of flesh.*—Medium red, near 43A; lightening toward center.
- *Evenness of color of flesh.*—Even.
- *Sweetness.*—Medium.
- *Acidity.*—Strong.
- *Time of flowering.*—Medium.
- *Time of ripening.*—Medium.
- *Type of bearing.*—Not remonstrant.
- *Chilling.*—Weak.

Planting date: Oct. 23, 2000.
10% flowering: Dec. 12, 2000.
First mature fruits: Jan. 23, 2001.
Maturity (15–20 gms/plant): Feb. 10, 2001.

Time of flowering date: Date of planting: Oct. 23, 2000 in the farm of La Mogalla, in Cartaya (Huelva), Spain, about 7° W, 37° N, 45 feet elevation. Ten percent (10%) flowering occurs about Dec. 12, 2000 with first mature fruit about Jan. 22, 2001 and maturity (15–20 g/plant) about Feb. 8, 2001.

Time of flowers (50% of plants at first flower): about Dec. 22, 2000.

Storage Qualities: 'Plahuelfre' fruit maintain their quality characteristics when keeping them in a frigo chamber at temperatures of about 2° C. during 48 hours. The fruit's color remains substantially the same.

Time of ripening: After planting as aforesaid, plants are grown in raised beds under tunnel (small tunnel with small holes in plastic walls). Water and fertilizer were applied through drip irrigation. Time of ripening (50% of plants with ripe fruit) is about January $28^{th}$. First mature fruit is about January $2^{nd}$ and maturity (15–20 gms/plant) is about February $8^{th}$.

General: The growing period in Huelva, Spain, where the observations were made is between about December $10^{th}$ and May $15^{th}$ of each year, with a maximum production at about mid-April. 'Plahuelfre' is a short variety that benefits from induction to flowering by chilling, usually a few hours sufficient, preferably at temperatures of 7° C. or less. Normally, the minimum number of hours is accumulated in the field during several days.

Disease resistance: No particular sensitivity to any disease or parasite has been observed for 'Plahuelfre'.

I claim:

1. A new and distinct strawberry plant of the variety substantially as shown and described.

* * * * *

96.09.014